United States Patent [19]
Leise, Jr. et al.

[11] Patent Number: 5,618,276
[45] Date of Patent: Apr. 8, 1997

[54] OSTOMY APPLIANCE WITH CONVEX PRESSURE RING

[75] Inventors: Walter F. Leise, Jr., Lindenhurst; Michael A. Metz, Chicago, both of Ill.

[73] Assignee: Hollister Incorporated, Libertyville, Ill.

[21] Appl. No.: 601,451

[22] Filed: Feb. 14, 1996

[51] Int. Cl.⁶ .................................................. A61F 5/44
[52] U.S. Cl. ........................ 604/336; 604/338; 604/344
[58] Field of Search ........................... 604/332, 336–344

[56] References Cited

U.S. PATENT DOCUMENTS

| | | |
|---|---|---|
| 3,339,546 | 9/1967 | Chen . |
| 3,523,534 | 8/1970 | Nolan . |
| 4,219,023 | 8/1980 | Galindo . |
| 4,738,257 | 4/1988 | Meyer et al. . |
| 4,834,731 | 5/1989 | Nowak et al. ........................... 604/339 |
| 5,330,454 | 7/1994 | Klingler et al. ........................ 604/338 |

OTHER PUBLICATIONS

WO 95/24169, published Sep. 14, 1995 based on PCT/DK95/00114 filed Mar. 10, 1995.

Primary Examiner—Robert A. Clarke
Attorney, Agent, or Firm—Tilton Fallon Lungmus

[57] ABSTRACT

An ostomy appliance is provided in which a thermoplastic convex pressure ring also functions as a belt-attachment ring. The pressure ring is directly and sealingly secured on its convex side to an adhesive faceplate and is also directly and sealingly secured on its opposite side to a collection pouch. Only two annular attachment zones, either in the form of heat seals or adhesive seals, are required to secure the pouch, pressure ring and faceplate together.

11 Claims, 1 Drawing Sheet

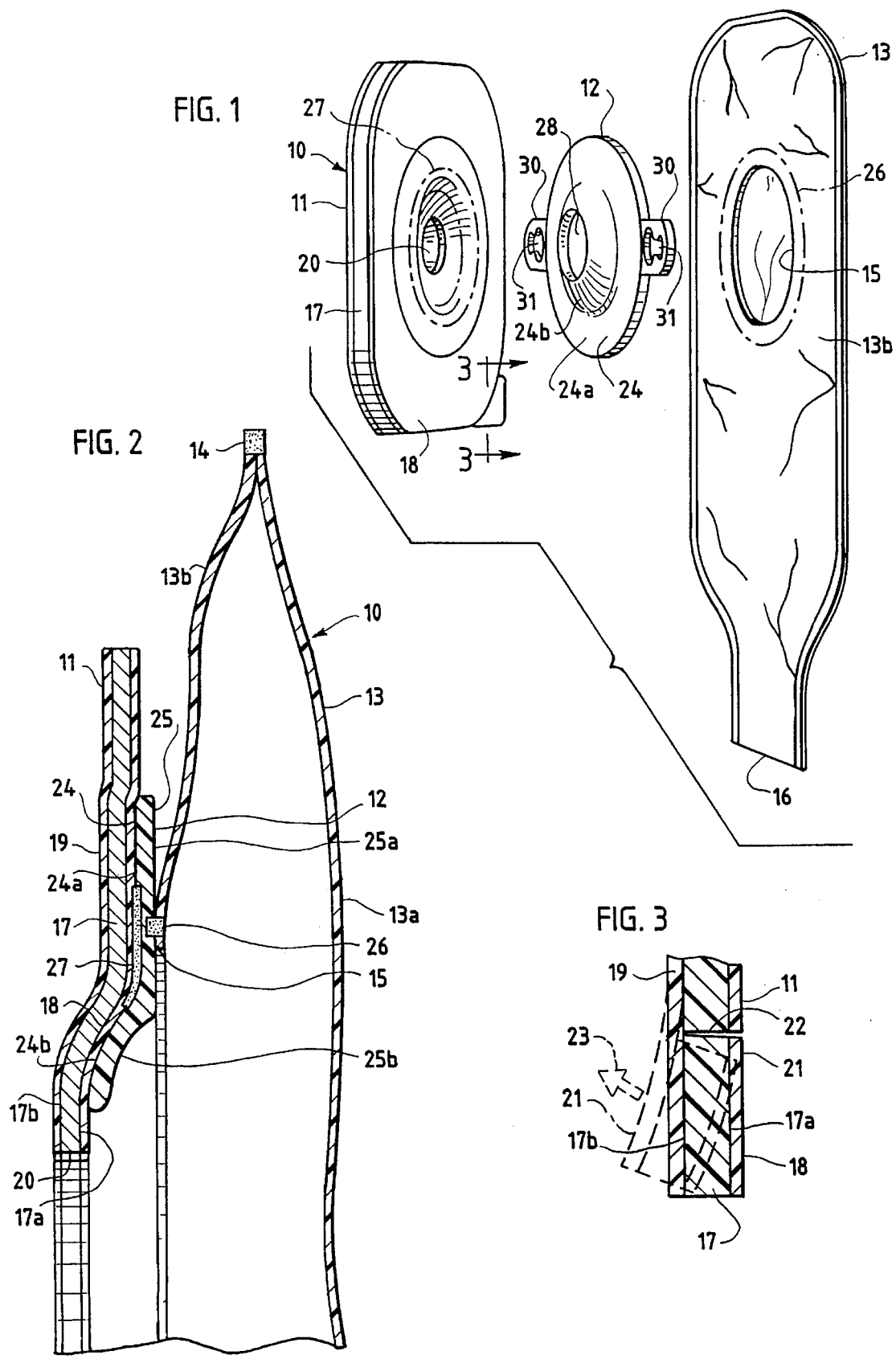

OSTOMY APPLIANCE WITH CONVEX PRESSURE RING

BACKGROUND AND SUMMARY

For ostomy patients with flush or recessed stomas, it has been found that if external pressure is applied in the peristomal region, sufficient protrusion of the stoma may occur to aid in the discharge of effluent directly into a collection pouch, thereby prolonging the effectiveness of the adhesive seal between the faceplate and the peristomal skin surfaces. Skin irritation and patient discomfort may also be greatly reduced.

In some cases, such pressure has been applied by means of a sealing ring formed of karaya or other soft, pliable, skin barrier material, but the deformability and cold-flowability of such a ring limits its effectiveness, or at least the duration of its effectiveness, in achieving adequate stomal protrusion. Some manufacturers of ostomy appliances have therefore introduced relatively rigid convex annular inserts or attachments for use with the adhesive faceplates of ostomy appliances. Galindo U.S. Pat. No. 4,219,023 discloses a convex insert with retaining tabs 54 for engaging the wall of a pouch 4 and a mounting member 16 to deform an annular cushion member 24 and produce stomal protrusion. However, attachment of the convex insert requires it to be sufficiently flexible so that it can be folded upon itself for insertion through the stoma-receiving opening of a pouch (or through a large drain opening at the bottom of such a pouch) and for interlocking its tabs with the edges of the pouch opening. In addition to the inconvenience associated with the insertion and attachment of such a pressure ring, there is the further disadvantage that such a ring might become disconnected in use and fail to perform its intended function.

Other constructions are known in which convex pressure ring assemblies are located along the bodyside surfaces of adhesive faceplates (see, for example, Nowak et al U.S. Pat. No. 4,834,731). While such an external construction avoids the aforementioned problems associated with the use of internal pressure rings, external arrangements tend to be relatively complex and require multiple seals between their various components. Reference may also be had to Klingler et al U.S. Pat. No. 5,330,454 which discloses a unitary ostomy appliance having a convex pressure ring, a belt attachment ring, and multiple seals between different elements of the assembly. In general, constructions that require a multiplicity of elements and seals between them not only incur greater manufacturing costs but might conceivably present increased risks of seal failure in use.

One aspect of this invention therefore lies in providing a one-piece ostomy appliance of relatively simple construction in which a single thermoplastic ring serves both as a convex pressure ring and as a belt attachment ring and in which only two concentric seals are required to join the pressure ring to both a pouch and an adhesive faceplate. Since the pressure ring is intended to be attached to a supporting belt, the pressure ring is particularly effective in distributing forces about a stoma to cause stomal protrusion as the supporting belt is tightened. The fact that only two seals are required to join the three components of the assembly together simplifies manufacturing procedures and results in cost benefits. Also, because failure (leakage) of ostomy appliances is believed to occur most frequently along seal lines or bonding zones, the provision of only two such zones is believed advantageous in terms of increased reliability and duration of possible use.

Briefly, the appliance comprises a collection pouch, an adhesive faceplate having a soft, elastomeric backing layer, and a relatively stiff convex pressure ring. The pressure ring has a first surface that faces the faceplate and includes a convex annular portion that engages the faceplate and supports the faceplate's annular inner portion in convex condition. The first surface of the pressure ring is sealingly secured to the backing layer of the faceplate along a first annular attachment zone and its second surface sealingly secured along a second annular attachment zone directly to the collection pouch about its stoma-receiving opening. In addition, the pressure ring is provided with a pair of integral and diametrically disposed belt-attachment tabs that project laterally from the ring and serve as connecting loops for the attachment of a support belt or strap.

Other features, advantages and objects of the invention will become apparent from the specification and drawings.

DRAWINGS

FIG. 1 is an exploded perspective view of an ostomy appliance embodying this invention.

FIG. 2 is an enlarged vertical sectional view of the appliance.

FIG. 3 is a still further enlarged fragmentary sectional view taken along line 3—3 of FIG. 1.

DETAILED DESCRIPTION OF PREFERRED EMBODIMENT

Referring to the drawings, the numeral 10 generally designates an ostomy appliance of a type generally known as a one-piece appliance. The term "one-piece" is here used to mean an appliance that is supplied to users in a unitary condition with the faceplate and pouch permanently connected to each other, in contrast to a so-called two-piece appliance in which a faceplate and pouch are separable, allowing a wearer to remove a used pouch from a faceplate and replace it with a fresh one.

Appliance 10 includes an adhesive faceplate 11, a thermoplastic pressure ring 12, and a pouch 13. The pouch is conventional and includes walls 13a and 13b of low-density polyethylene or any other thin, flexible film that is impermeable to liquids and is capable of being heat sealed to compatible thermoplastic materials. A particularly suitable material is believed to be polyethylene coextruded with a coextensive layer or core of polyvinylidene chloride, such material being commercially available under the designation Saranex from Dow Chemical Company, Midland, Mich.

The walls 13a and 13b are sealed together along their peripheral edges by heat seal bond 14, and the bodyside wall 13b has a stoma-receiving opening 15. If desired, a drain opening 16 may be provided at the pouches' lower end with such opening being closed by a suitable clamp as disclosed, for example, in Nolan U.S. Pat. No. 3,523,534. Alternatively, the pouch may be provided with a drain valve (see Jensen U.S. Pat. No. 4,280,498), or may be completely sealed at its lower end.

Faceplate 11 includes an adhesive layer 17 and a soft, elastomeric backing layer 18. While medical grade pressure-sensitive adhesives, usually acrylic adhesives, have been commonly used for ostomy faceplates, and may be used here, recent products have utilized moisture-absorbing, hydrocolloid-containing skin barrier materials for adhesive attachment of faceplates. Such materials are considered skin-friendly because they are generally non-allergenic, absorb moisture from the skin and, following a normal interval of use, are of sufficiently reduced tackiness that they may be easily peeled away without damaging or irritating the skin.

One skin-friendly adhesive barrier material is disclosed in U.S. Pat. No. 3,339,546 and consists essentially of a blend of water-soluble and swellable hydrocolloids such as powdered pectin, gelatin and carboxymethylcellulose in a water-insoluble viscous gum-like elastic binder such as natural rubber, silicone rubber, polyurethane rubber, or (notably) polyisobutylene. Tackifiers, plasticizers and other additives may be included to vary the properties of such compositions. In such a hydrocolloid-containing barrier composition, the elastomer constitutes a continuous phase and the hydrocolloid or hydrocolloids are dispersed therein in particulate form. As the hydrocolloids absorb moisture, such a composition swells and begins to lose its integrity. Steps may be taken to retard or prevent barrier disintegration or dissolution, such as incorporating a polymer capable of being cross-linked by irradiation (see U.S. Pat. Nos. 4,477,325 and 4,738,257). Other barrier compositions that resist disintegration/dissolution have been formulated in which the continuous phase includes a physically cross-linked elastomer consisting of one more styrene-olefin, styrene block copolymers, a hydrocarbon tackifier resin, and an antioxidant, and a disperse phase consisting of one or more water-swellable hydrocolloids (see U.S. Pat. No. 4,867,748).

The backing layer 18 extends along the bodyside surface 17a of the adhesive layer 17 and is composed of a soft, resilient, liquid and gas impermeable, elastomeric material. A resilient foam of polyethylene, polyurethane, or other polymeric material having similar properties is believed particularly suitable. While any thermoplastic foam having such characteristics may be used, particularly effective results have been obtained using a close-cell polyethylene foam. The foam layer 18 is secured to the barrier layer 17 by the adhesive properties of the skin barrier material.

One characteristic of such skin barrier materials is the tendency to flow or migrate in response to deforming forces, so a function of the foam backing layer 18 is to limit such migration or flow of the barrier layer. Also, because of the stretchability and recoverability of the elastomeric backing material, layer 18 tends to restore the shape of layer 17 when distorting forces are removed or reduced. The faceplate may therefore flex, expand and contract to conform with body contours and accommodate changes in such contours.

The bodyside surface 17b of the adhesive barrier layer 17 is covered by a removable protective release layer 19. The release layer may be formed of silicone coated paper or any other suitable material, although a plastic film of silicone-coated polyethylene or other suitable plastic material is believed particularly desirable.

Faceplate 11 has a central opening 20 that is aligned with the stoma-receiving opening 15 of pouch 13. Along its periphery, the faceplate also may be provided with a tab 21 to facilitate removal of release film 19 when the appliance is to be adhered to a patient. As shown in FIG. 3, the tab may be composed of the same three layers (adhesive layer 17, backing layer 18, release film 19) as the remainder of the faceplate; however, the tab is delineated in part by a slit 22 that extends only through the backing and adhesive layers (FIG. 3). A user may therefore grasp tab 21 and flex it in the direction of arrow 23 (FIG. 3) to commence removal of the release film 19 from the faceplate.

The pressure/attachment ring 12 is interposed between pouch 13 and faceplate 11 and has its opposite surfaces directly and sealingly bonded to both. Specifically, the ring has a first surface 24 that includes a generally planar outer portion 24a and an annular convex inner portion 24b. The ring's opposite or second surface 25 includes a planar outer portion 25a (that is generally parallel with outer portion 24a) and a concave annular inner portion 25b. The ring is stiff but still flexible and may be formed of any of a variety of polymeric materials capable of being bonded to both the faceplate and pouch. Polyolefins, particularly a blend of high and low density polyethylenes, have been found particularly effective, but other materials having similar properties may be used. As shown in the drawings, the ring has the outer portion 25a of its second surface 25 heat sealed directly to the pouch along an annular zone of attachment 26 surrounding the pouches' stoma-receiving opening 15. so that, for example, the ring may be curved or bent with sufficient finger pressure and the belt-attachment tabs 30 (hereafter described) may be flexed to conform generally with abdominal curvatures when a connecting belt is tightened about a wearer's body. Polyolefins, particularly a blend of high and low density polyethylenes, have been found particularly effective, but other materials having similar properties may be used.

As shown in the drawings, the ring has the outer portion 25a of its second surface 25 heat sealed directly to the pouch along an annular zone of attachment 26 surrounding the pouches' stoma-receiving opening 15. The bodyside surface 24 of the pressure ring similarly has its outer portion 24a bonded along annular attachment zone 27 to the backing film 18 of the faceplate. Seal 27 might conceivably take the form of a heat seal similar to seal 26; however, it has been found advantageous to form seal 27 as a hot-melt adhesive seal that may therefore be formed to secure the pressure ring to the faceplate after the pressure ring has already been attached to the pouch. It is for that reason that a blend of high and low density polyethylenes is considered particularly suitable as the composition for the pressure ring, because we have discovered that the low density component renders the ring readily heat sealable or weldable to the pouch material, and the high density component renders the ring amenable to attachment to the faceplate by any suitable hot melt adhesive that is both flexible and pressure sensitive at room temperature. Such adhesives are well known and commercially available, as are polyethylenes of high and low density as those terms are commonly used in the industry. A blend by weight percent of 50% high density polyethylene and 50% low density polyethylene has been found particularly effective, but other proportions comprising about 35% to 65% high density polyethylene and about 65% to 35% low density polyethylene are believed suitable.

The sealing zones 26 and 27 are depicted on the pouch and faceplate in phantom in the exploded view of FIG. 1. The faceplate 11 is shown to be recessed in FIG. 1 with such recess conforming to the size and shape of the convex surface 24b of the pressure ring. It is to be understood, however, that such recess is shown only for clarity of illustration and is not meant to suggest that the faceplate must be preformed with a recess prior to being attached to the pressure plate. While the faceplate may indeed be so preformed, it has been found that because of its softness, pliability and conformability, the faceplate may assume a planar configuration prior to its attachment to the pressure ring and that the force exerted to seal the parts together is sufficient to cause the faceplate to assume the contoured configuration depicted in the drawings.

The pressure ring 12 has a central opening 28 coaxial with the openings of the faceplate and pouch. Opening 28 is substantially smaller than pouch opening 15 and is preferably slightly larger than faceplate opening 20.

A pair of laterally-facing and diametrically-disposed belt-attachment tabs 30 project outwardly from opposite edges of the pressure ring 12. The tabs are formed integrally with the ring and are provided with openings 31 for receiving the connectors of a conventional support belt or strap (not shown).

In a preferred embodiment, ring 12 therefore performs dual functions as a support ring and as a convex pressure ring. The laterally projecting tabs or ears 30 transmit force from a belt directly to the remainder of the pressure ring, resulting in what is believed to be a generally uniform application of pressure to the skin surfaces surrounding a patient's stoma. The belt ring (pressure ring), being welded to the pouch, insures that the pouch will be held in place when the belt is tightened.

While in the foregoing, we have disclosed an embodiment of the invention in considerable detail for purposes of illustration, it will be understood by those skilled in the art that many of these details may be varied without departing from the spirit and scope of the invention.

We claim:

1. A one-piece ostomy appliance comprising a collection pouch having side walls of thermoplastic film; one of said walls having a stoma-receiving opening therein; a soft, flexible adhesive faceplate for adhesive attachment to a patient; said faceplate having a stoma-receiving opening aligned with the opening of said pouch and having an adhesive bodyside layer and a flexible backing layer; a relatively stiff thermoplastic pressure ring having an opening aligned with the stoma-receiving openings of said pouch and faceplate and having a first surface facing said faceplate and an opposite second surface facing said pouch; said first surface having a convex annular portion immediately surrounding said opening of said ring and engaging said faceplate to maintain an annular portion of said faceplate in convex conformity with said ring; said first surface of said pressure ring being sealingly secured along a single first annular attachment zone directly to said backing layer of said faceplate and said second surface of said pressure ring being sealingly secured directly to said pouch along a second annular attachment zone located along a portion of said second surface directly opposite from said first attachment zone.

2. The appliance of claim 1 in which said pressure ring has a pair of integral and diametrically-disposed belt-attachment tabs projecting laterally therefrom.

3. The appliance of claims 1 or 2 in which said flexible backing layer is composed of an elastomeric foam.

4. The appliance of claims 1 or 2 in which said first surface of said pressure ring is sealingly secured to said backing layer of said faceplate along said first annular attachment zone by means of a hot-melt adhesive.

5. The appliance of claim 4 in which said second surface of said pressure ring is sealingly secured to said pouch along said second annular attachment zone by means of a heat seal.

6. The appliance of claim 5 in which said pressure ring is composed of a blend of high and low density polyethylenes and said hot melt adhesive is flexible and pressure sensitive at room temperature.

7. The appliance of claim 6 in which said blend comprises about 35 to 65 percent high density polyethylene and about 65 to 35 percent low density polyethylene.

8. The appliance of claim 7 in which said blend comprises about equal proportions by weight of high and low density polyethylene.

9. The appliance of claims 1 or 2 in which said stoma-receiving opening of said pouch is substantially larger than said stoma-receiving opening of said faceplate.

10. The appliance of claim 9 in which said opening of said pressure ring is larger than said stoma-receiving opening of said faceplate and substantially smaller than said stoma-receiving opening of said pouch.

11. The appliance of claims 1 or 2 in which said adhesive bodyside layer of said faceplate is composed of a soft, pliant, hydrocolloid-containing skin barrier material having both wet and dry tack.

\* \* \* \* \*